(12) United States Patent
Sarabia et al.

(10) Patent No.: US 11,534,579 B2
(45) Date of Patent: Dec. 27, 2022

(54) STEERABLE INTRODUCER SHEATH ASSEMBLY

(71) Applicant: 510 Kardiac Devices, Inc., Mableton, GA (US)

(72) Inventors: Jaime Eduardo Sarabia, Mableton, GA (US); David Scott Lim, Keswick, VA (US); Alfred Raschdorf, St. James, NY (US)

(73) Assignee: 510 Kardiac Devices, Inc., Mableton, GA (US)

( * ) Notice: Subject to any disclaimer, the term of this patent is extended or adjusted under 35 U.S.C. 154(b) by 481 days.

(21) Appl. No.: 14/987,272

(22) Filed: Jan. 4, 2016

(65) Prior Publication Data

US 2016/0193449 A1 Jul. 7, 2016

Related U.S. Application Data (60) Provisional application No. 62/099,409, filed on Jan. 2, 2015.

(51) Int. Cl.
*A61M 25/01* (2006.01)
*A61M 25/06* (2006.01)

(52) U.S. Cl.
CPC .... *A61M 25/0147* (2013.01); *A61M 25/0136* (2013.01); *A61M 25/0662* (2013.01)

(58) Field of Classification Search
CPC .......... A61M 25/0147; A61M 25/0136; A61M 25/0662; A61M 25/0133; A61M 25/00; A61M 25/0144; A61M 25/0014; A61M 2025/015; A61M 2025/0161; A61M 25/01; A61M 25/0102; A61M 25/0105; A61M 25/015; A61M 25/0169; A61M 25/0172;

(Continued)

(56) References Cited

U.S. PATENT DOCUMENTS 4,815,476 A * 3/1989 Clossick ................ A61B 10/00
600/564
5,117,839 A * 6/1992 Dance ............... A61M 25/0136
600/434

(Continued)

FOREIGN PATENT DOCUMENTS

EP 1759668 3/2007

OTHER PUBLICATIONS

Extended European Search Report dated May 8, 2017 for Application No. EP 17150100.

*Primary Examiner* — Kevin C Sirmons
*Assistant Examiner* — Alexandra Lalonde
(74) *Attorney, Agent, or Firm* — Nelson Mullins Riley & Scarborough LLP (57) ABSTRACT

An introducer sheath assembly having a handle portion including a front end and a rear end, and a introducer sheath extending outwardly from the front end of the handle portion, the introducer sheath including a device lumen configured to slidably receive a corresponding device, a guidewire lumen configured to slidably receive a corresponding guidewire, a first steering cable lumen, a second steering cable lumen, a first steering cable disposed in the first steering cable lumen and a second steering cable disposed in the second steering cable lumen, wherein the first steering cable lumen, the second steering cable lumen and the guidewire lumen are disposed radially outwardly from the device lumen.

18 Claims, 12 Drawing Sheets

(58) Field of Classification Search
CPC .......... A61M 25/09; A61M 2025/0175; A61M 2025/0177; A61M 2025/09116; A61M 2025/09125; A61M 25/0097; A61B 2018/00916; A61B 10/06; A61B 2017/2946; A61B 17/2909; A61B 1/0057; A61B 2017/00318; A61B 2017/00323; A61B 2017/00327; A61B 1/0052
See application file for complete search history.

(56) References Cited

U.S. PATENT DOCUMENTS

| | | | | |
|---|---|---|---|---|
| 6,120,476 | A * | 9/2000 | Fung | A61B 18/1492 604/528 |
| 6,450,948 | B1 | 9/2002 | Matsuura et al. | |
| 2005/0065397 | A1 * | 3/2005 | Saadat | A61B 1/0055 600/104 |
| 2005/0107737 | A1 * | 5/2005 | McDaniel | A61M 25/0136 604/95.04 |
| 2009/0254083 | A1 * | 10/2009 | Wallace | A61B 18/1482 606/41 |
| 2009/0287188 | A1 * | 11/2009 | Golden | A61M 25/0147 604/528 |
| 2013/0030519 | A1 * | 1/2013 | Tran | A61F 2/2433 623/2.11 |
| 2014/0051987 | A1 * | 2/2014 | Kowshik | A61B 5/06 600/424 |
| 2014/0088497 | A1 * | 3/2014 | Campbell | A61M 25/0136 604/95.04 |
| 2015/0025507 | A1 * | 1/2015 | Golden | A61M 25/0028 604/523 |
| 2015/0057610 | A1 * | 2/2015 | Osypka | A61B 17/3468 604/95.04 |
| 2015/0231366 | A1 | 8/2015 | Davies et al. | |
| 2016/0338571 | A1 * | 11/2016 | Haraguchi | A61B 1/0057 |

* cited by examiner

STEERABLE INTRODUCER SHEATH ASSEMBLY

CLAIM OF PRIORITY

This application claims priority to U.S. Provisional Application No. 62/099,409, filed Jan. 2, 2015, the entire disclosure of which is incorporated by reference herein.

FIELD OF THE INVENTION

The present disclosure relates generally to medical devices and, more specifically, to vascular access sheaths and catheters.

BACKGROUND

Increasingly, minimally-invasive, catheter-based therapies are being developed that allow physicians to provide therapies to patients whose existing comorbidities may preclude them from having a needed, but more invasive, surgical procedure. Over the last 30-plus years, catheter based procedures that involve puncturing/crossing the interatrial septum, such as cardiac ablation and balloon valvuloplasty have become commonplace. In the last 5 to 10 years, new structural heart procedures, such as transcatheter valve repair/replacement, and left atrial appendage occlusion, have gained regulatory approvals and have become increasingly common procedures performed in the cardiac catheterization laboratory or hybrid operating room. With the advent of these technologies has come an increase in the need for structural heart interventionalists (specialty physicians who perform these types of procedures) to engage and cross the interatrial septum in the heart.

Historically, crossing the septum has been the purview of pediatric cardiologists or electrophysiologists due to the prevalence of cardiac ablation procedures which require crossing the interatrial septum. However, interventional cardiologists are increasingly starting to provide therapy to the left side of the heart and the requirement to puncture the ineteratrial septum and provide these new therapies is increasing. Unfortunately, many of these interventional cardiologists do not perform a transseptal puncture with enough regularity to become proficient at it. For these left-sided procedures, safely puncturing the interatrial septum and gaining access to the left side of the heart is not enough. These new technologies demand a very specific and safe location when crossing the interatrial septum. Additionally, crossing the interatrial septum has been historically guided by fluoroscopy (X-ray), and more recently by echocardiographic ultrasound (intracardiac echocardiography, transephogeal echocardiography or transthoracic echocardiography). Fluoroscopy is limited in its role due to its limited ability to image soft tissue, such as the interatrial septum. Therefore, echocardiography is increasingly being relied upon to guide these types of procedures.

As such, it is desirable to provide these newly evolving structural heart interventionalists with a tool to help them safely and accurately cross the interatrial septum. Preferably, these tools may have features that increase their utility with echocardiographic imaging, and may enhance the echocardiographic information or facilitate certain modalities of echocardiography to be used for image guidance that might not otherwise be useful.

The present invention recognizes and addresses considerations of prior art constructions and methods.

SUMMARY

One embodiment of an introducer sheath assembly in accordance with the present disclosure includes a handle portion with a front end and a rear end, and a introducer sheath extending outwardly from the front end of the handle portion, the introducer sheath including a device lumen configured to slidably receive a corresponding device, a guidewire lumen configured to slidably receive a corresponding guidewire, a first steering cable lumen, a second steering cable lumen, a first steering cable disposed in the first steering cable lumen and a second steering cable disposed in the second steering cable lumen, wherein the first steering cable lumen, the second steering cable lumen and the guidewire lumen are disposed radially outwardly from the device lumen.

Another embodiment of an introducer sheath assembly in accordance with the present disclosure includes a handle portion with a front end and a rear end, a introducer sheath extending outwardly from the front end of the handle portion, the introducer sheath including a device lumen configured to slidably receive a corresponding device, a first steering cable lumen, a first steering cable disposed in the first steering cable lumen, a first gear assembly disposed in the handle portion, a proximal end of the first steering cable being fixed to the first gear assembly, and a drive gear assembly disposed in the handle portion, wherein the drive gear assembly engages the first gear assembly so that the first gear assembly and the drive gear assembly rotate simultaneously.

Another embodiment of an introducer sheath assembly in accordance with the present disclosure includes a handle portion with a front end and a rear end, a introducer sheath extending outwardly from the front end of the handle portion, the introducer sheath including a device lumen configured to slidably receive a corresponding device, and a device locking assembly disposed at the rear end of the housing portion, including an elongated stem defining an axially extending bore that is confirmed to slidably receive the corresponding device, the elongated stem being axially movable with respect to the handle portion, a clamp disposed on the distal end of the elongated stem, the clamp being positionable between a locked position in which the corresponding device is axially fixed with respect to the elongated stem and an un-locked position in which the corresponding device is slidable within the axially extending bore of the elongated stem.

BRIEF DESCRIPTION OF THE DRAWINGS

The accompanying drawings, which are incorporated in and constitute a part of this specification, illustrate one or more embodiments of the invention and, together with the description, serve to explain the principles of the invention.

A full and enabling disclosure of the present invention, including the best mode thereof, directed to one of ordinary skill in the art, is set forth in the specification, which makes reference to the appended drawings, in which.

Repeat use of reference characters in the present specification and drawings is intended to represent same or analogous features or elements of the invention according to the disclosure.

DETAILED DESCRIPTION OF THE PREFERRED EMBODIMENTS

Figure 1:
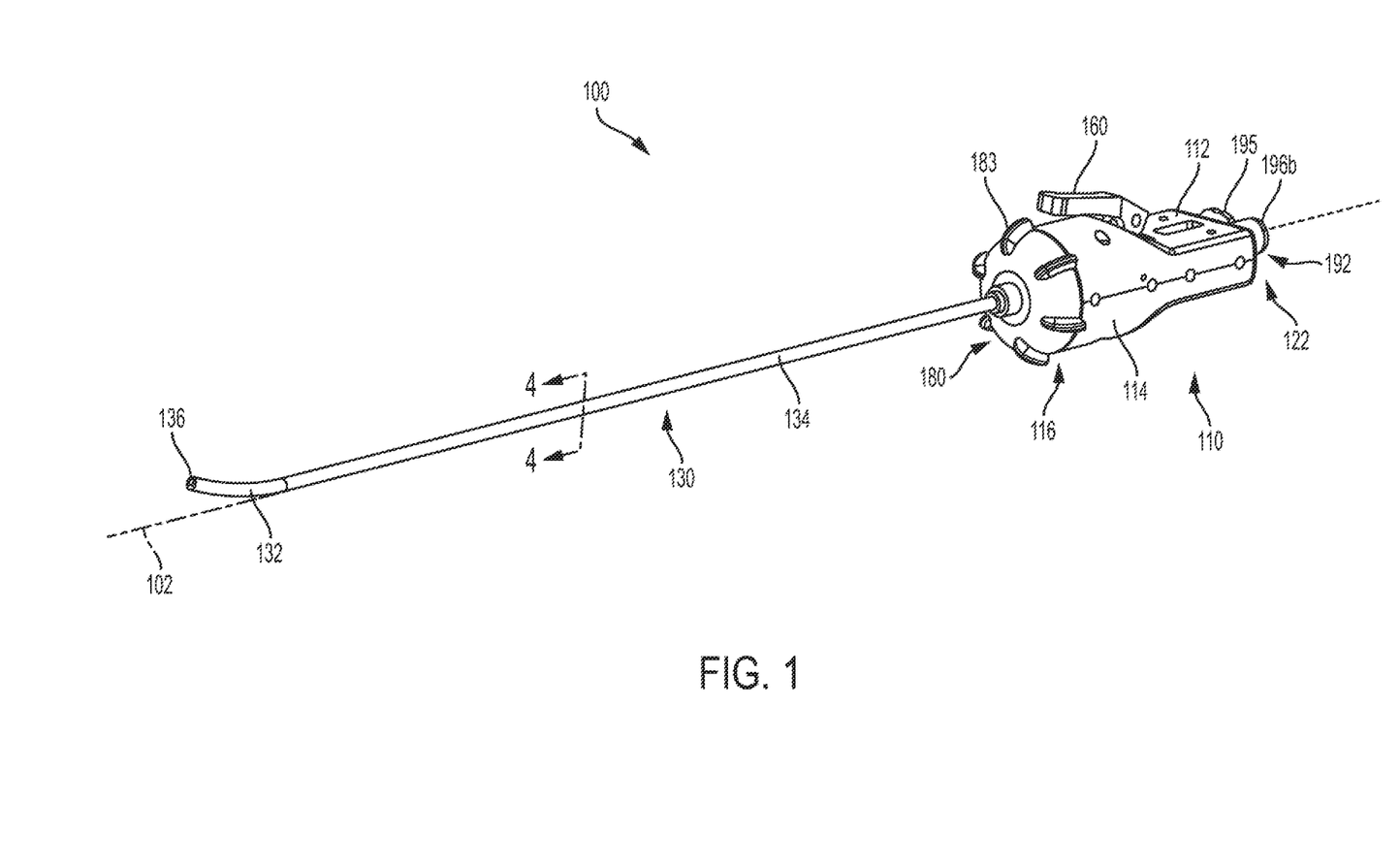
FIG. 1 is a top perspective view of a steerable introducer sheath assembly in accordance with an embodiment of the present disclosure.

Reference will now be made in detail to presently preferred embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents. As well, directions given for deflection of the distal portion of the introducer sheath of the present invention are given as left or right of a vertical plane that passes through longitudinal center axis 102 (FIG. 1) (202 in FIG. 8) of the disclosed introducer sheath assembly, when the introducer sheath is fully extended. Note, the introducer sheath assembly is, preferably, substantially symmetrical about the vertical plane.

Referring now to FIGS. 1 through 4, a steerable introducer sheath assembly 100 in accordance with an embodiment of the present disclosure includes a handle portion 110, an introducer sheath 130 extending outwardly from its front end 116, a steering lever 160 for manipulating introducer sheath 130, and a device locking assembly 192 for selectively securing a corresponding medical catheter device (not shown) within introducer sheath 130 in the desired position, as discussed in greater detail below.

Figure 7A:
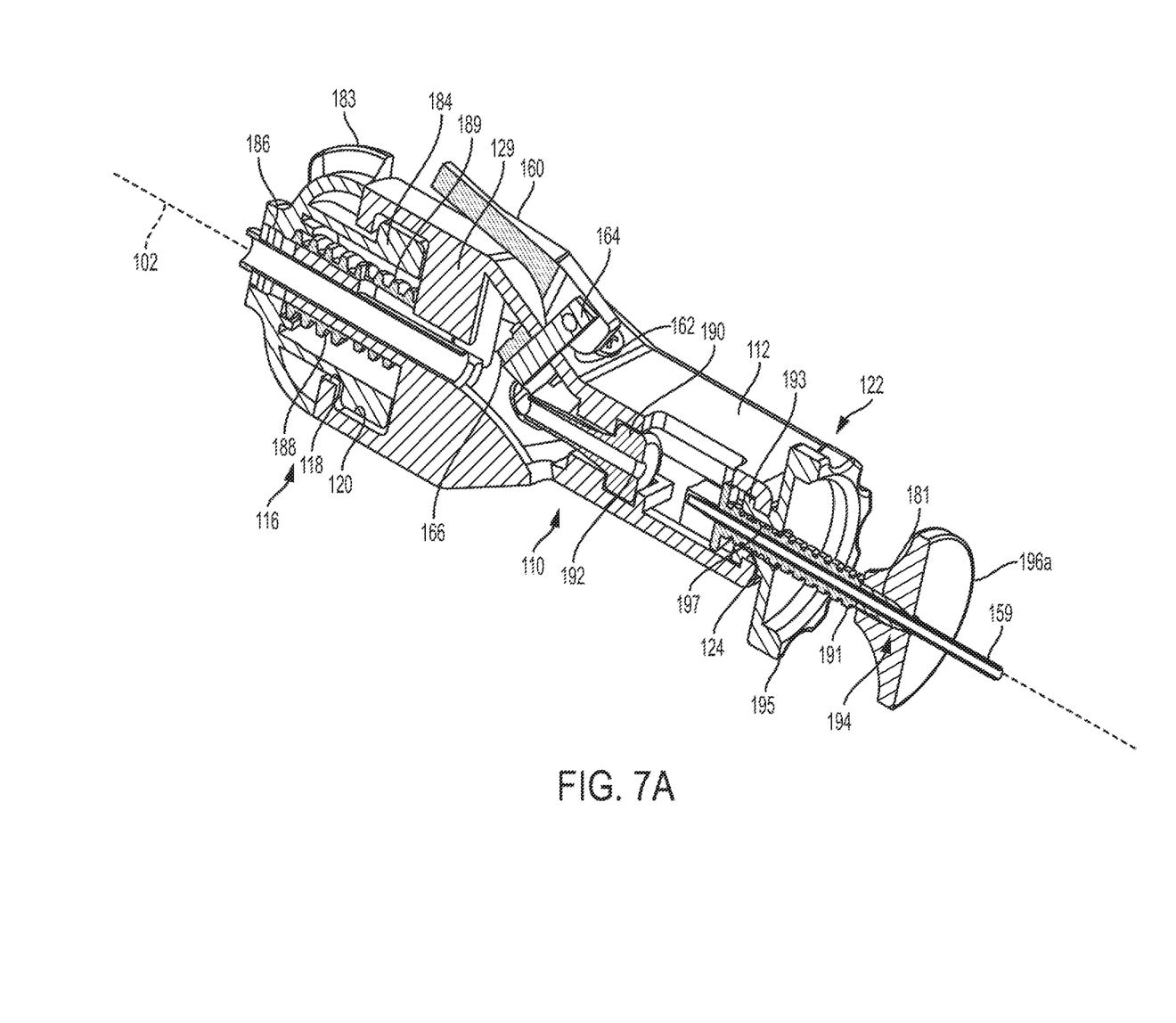
FIGS. 7A and 7B are perspective, cut-away views of the handle portion of the sheath assembly shown in FIG. 1, taken along line 7-7 of FIG. 6.

Referring additionally to FIG. 7A, handle portion 110 includes an upper housing portion 112 and a lower housing portion 114 that define a front aperture 118 disposed at its front end 116 and a rear aperture 124 disposed at its rear end 122. Front aperture 118 is configured to rotatably receive front end cap 180 so that front end cap 180 is free to rotate relative to handle portion 110. An outwardly depending radial flange 184 is disposed at a rear end of front end cap 180 and is rotatably received in an annular cavity 120 defined by handle portion 110. The diameter of radial flange 184 is greater than that of front aperture 118 so that front end cap 180 is axially retained within handle portion 110. A plurality of ridges 183 extend radially outwardly from the outer surface of front end cap 180 so that front end cap 180 may be readily grasped and rotated during use. Front end cap 180 includes an internally threaded portion 186 that is configured to engage a correspondingly threaded stem 188 that is disposed within handle portion 110.

As best seen in FIG. 7A, threaded stem 188 includes an axially extending slot 189 that is engaged by an axially extending flange 129 that depends radially inwardly from an inner surface of handle portion 110. As such, rotation of front end cap 180 relative to threaded stem 188 causes threaded stem 188 to move axially within handle portion 110, parallel to center axis 102, as rotation of the stem is prevented by the slot and flange combination. As discussed in greater detail below, the axial motion of threaded stem 188 that results from the rotation of front end cap 180 is utilized to affect the amount curvature of a distal portion 132 of introducer sheath 130 away from longitudinal center axis 102, within the vertical plane.

Figure 3:
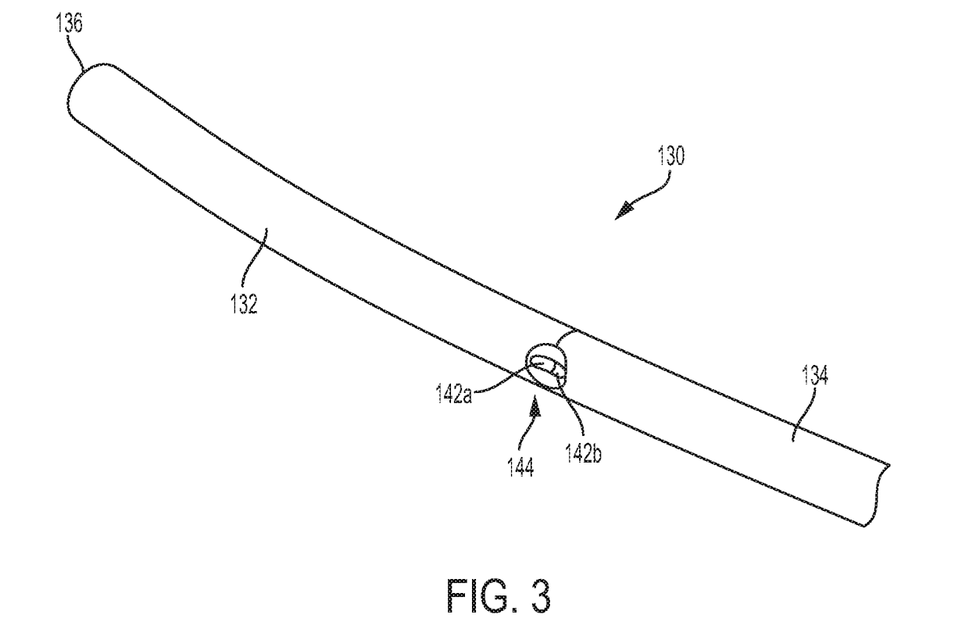
FIG. 3 is a perspective view of a distal end of the introducer sheath of the sheath assembly shown in FIG. 1.
Figure 4:
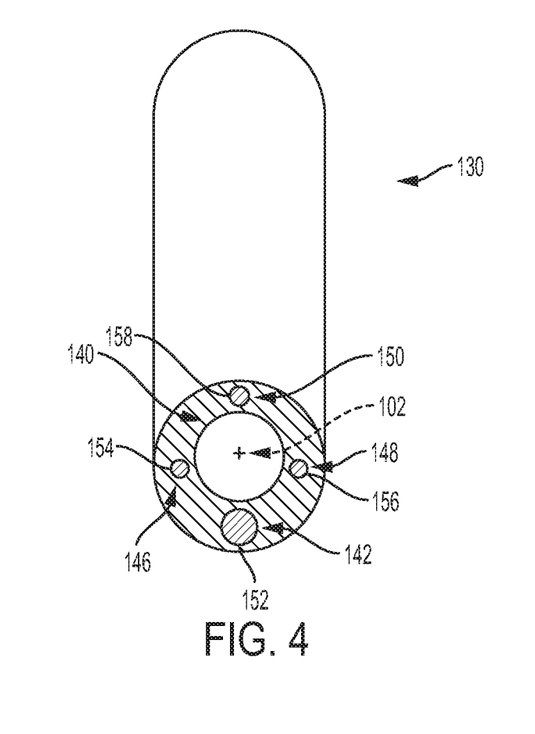
FIG. 4 is a cross-sectional view of the introducer sheath of the sheath assembly shown in FIG. 1, taken along line 4-4.

As best seen in FIGS. 3 and 4, introducer sheath 130 includes a distal portion 132 terminating in a distal tip 136, and a proximal portion 134 that extends from handle portion 110 to distal portion 132. As best seen in the cross-sectional view provided in FIG. 4, introducer sheath 130 preferably includes a centrally located device lumen 140 that is configured to slidably receive a corresponding catheter device 159 (FIG. 6), a guidewire lumen 142 that is configured to slidably receive a corresponding guidewire 152, first and second steering cable lumens 146 and 148 in which first and second steering cables 154 and 156 are disposed, respectively, and a third steering cable lumen 150 in which a third steering cable 158 is disposed. As shown, device lumen 140 slidably receives a dilator 159 (FIG. 6), which in turn is configured to slidably receive medical devices such as standard length Bayliss RF transeptal devices, available from Bayliss Medical, Montreal, Canada, and Brockenbrough transeptal catheters.

As shown, first, second and third steering cable lumens 146, 148 and 150, as well as guidewire lumen 142, are disposed radially outwardly of device lumen 140, with the third steering cable lumen 150 and guidewire lumen 142 being disposed above and below device lumen along the vertical plane in which longitudinal center axis 102 lies. As such, adjusting tension on third steering cable 152 will adjust the curvature of distal portion 132 of introducer sheath 130 within the vertical plane while minimizing any unwanted deflection of introducer sheath 130 to the left or right of the vertical plane. Similarly, first and second steering cable lumens 146 and 148 are disposed on opposite sides of device lumen 140, and are symmetric about a horizontal plane in which longitudinal center axis 102 lies, the horizontal and vertical planes being transverse to each other. As such, adjusting the tension in first and second steering cables 154 and 156 adjusts the deflection of the introducer sheath's distal portion 132 to the left or right of the vertical plane, while minimizing the potential unintended motion within the vertical plane. In short, when viewing sheath assembly 100 from the rear with introducer sheath 130 extending outwardly in an undeflected position, first steering cable 154 and second steering cable 156 are utilized to effect curvature of distal portion 132 of introducer sheath 130 to the left and to the right, respectively, whereas third steering cable 158 is utilized to adjust the amount of curvature of distal portion 132 of the introducer sheath 130 within the vertical plane.

Figure 2:
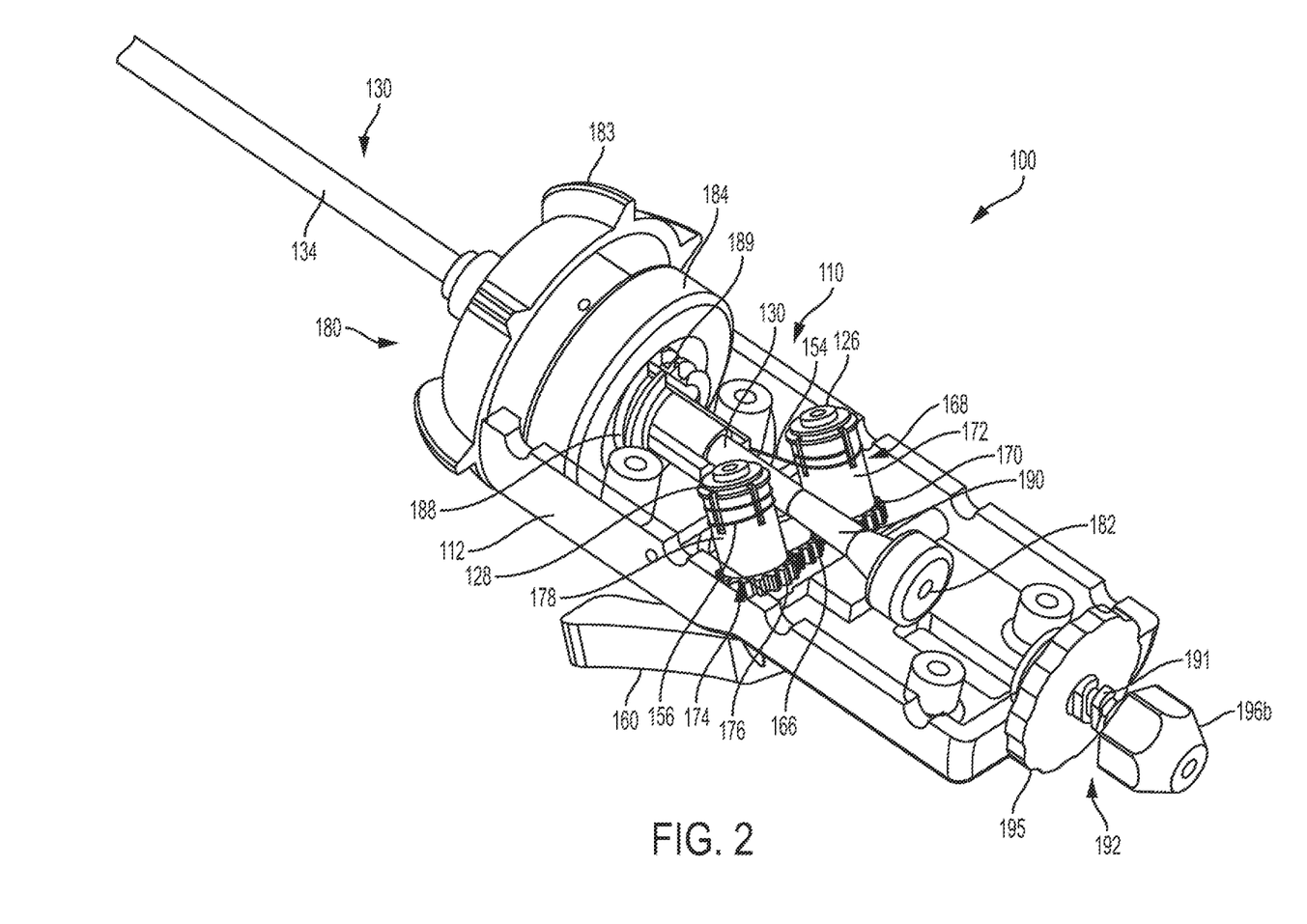
FIG. 2 is a partial, bottom perspective view of the sheath assembly shown in FIG. 1, with the bottom portion of the handle housing removed.

As best seen in FIGS. 2 and 7A, steering lever 160 is pivotably secured to a first end of a stem 164 that is non-rotatably secured to a drive gear 166 at its second end. As such, when viewing sheath assembly 100 from above, rotation of steering lever 160 in the clockwise (CW) or counter-clockwise (CCW) directions causes similar rotation of drive gear 166. As best seen in FIG. 2, a first gear assembly 168 is rotatably secured to a first post 126 that depends inwardly from upper housing portion 112, first gear assembly 168 including a first gear 170 and a barrel portion 172. Similarly, a second gear assembly 174 is rotatably secured to a second post 128 that depends inwardly from upper housing portion 112, second gear assembly 174 including a second gear 176 and a barrel portion 178. As shown, the distal end of first steering cable 154 is fixed to introducer sheath 130 at its distal tip 136, whereas the proximal end of first steering cable 154 is affixed to barrel portion 172 of first gear assembly 168. Similarly, the distal end of second steering cable 156 is affixed to introducer sheath 130 at its distal tip 136, whereas the proximal end of second steering cable 156 is affixed to barrel portion 178 of second gear assembly 174. Drive gear 166 is engaged with both first gear 170 and second gear 176 such that rotation of drive gear 166 causes first and second gear assemblies 168 and 174 to rotate simultaneously, thereby adjusting the tension applied to first and second steering cables 154 and 156.

Figure 5A:
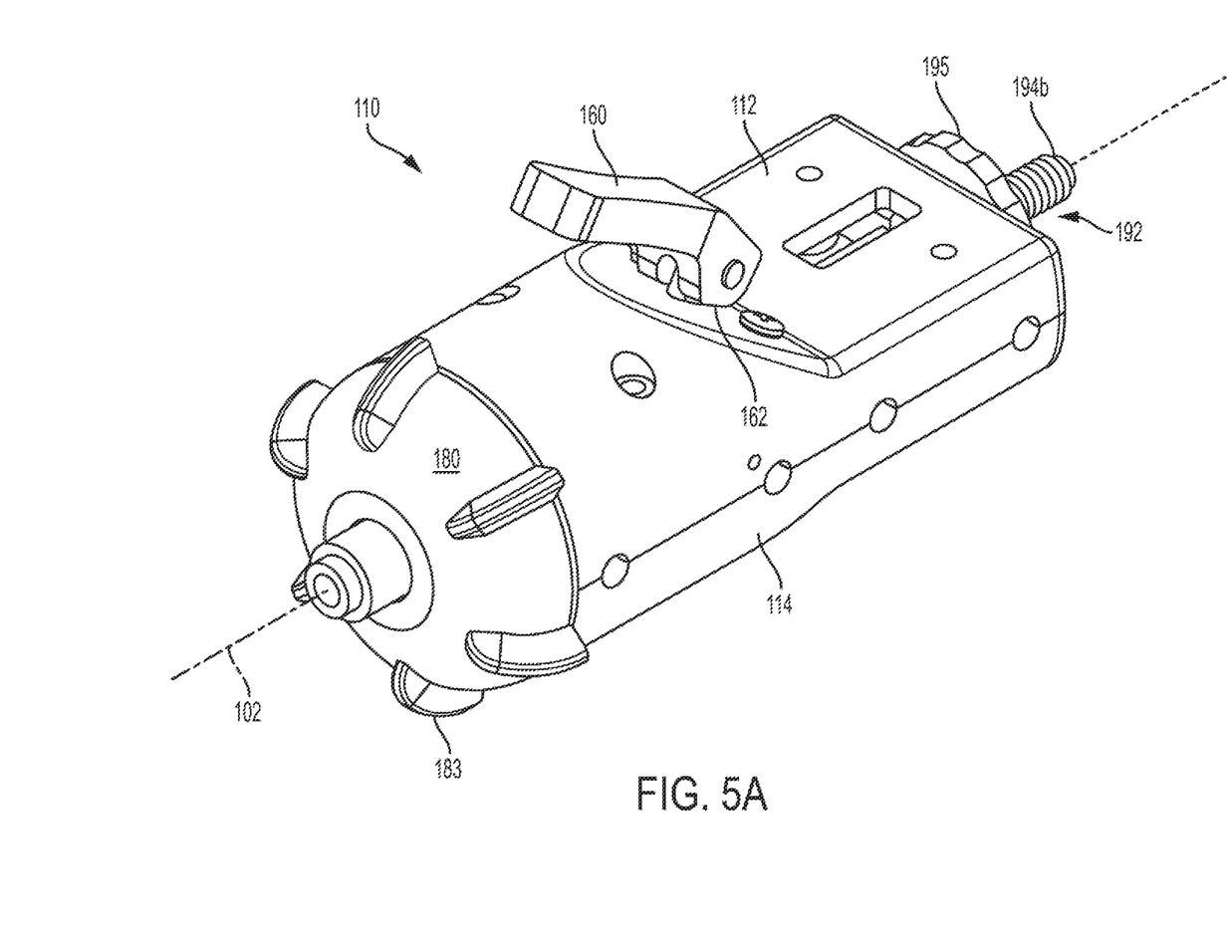
FIGS. 5A and 5B are top perspective views of the handle portion of the sheath assembly as shown in FIG. 1, with the steering lever in an unlocked and locked position, respectively.
Figure 5B:
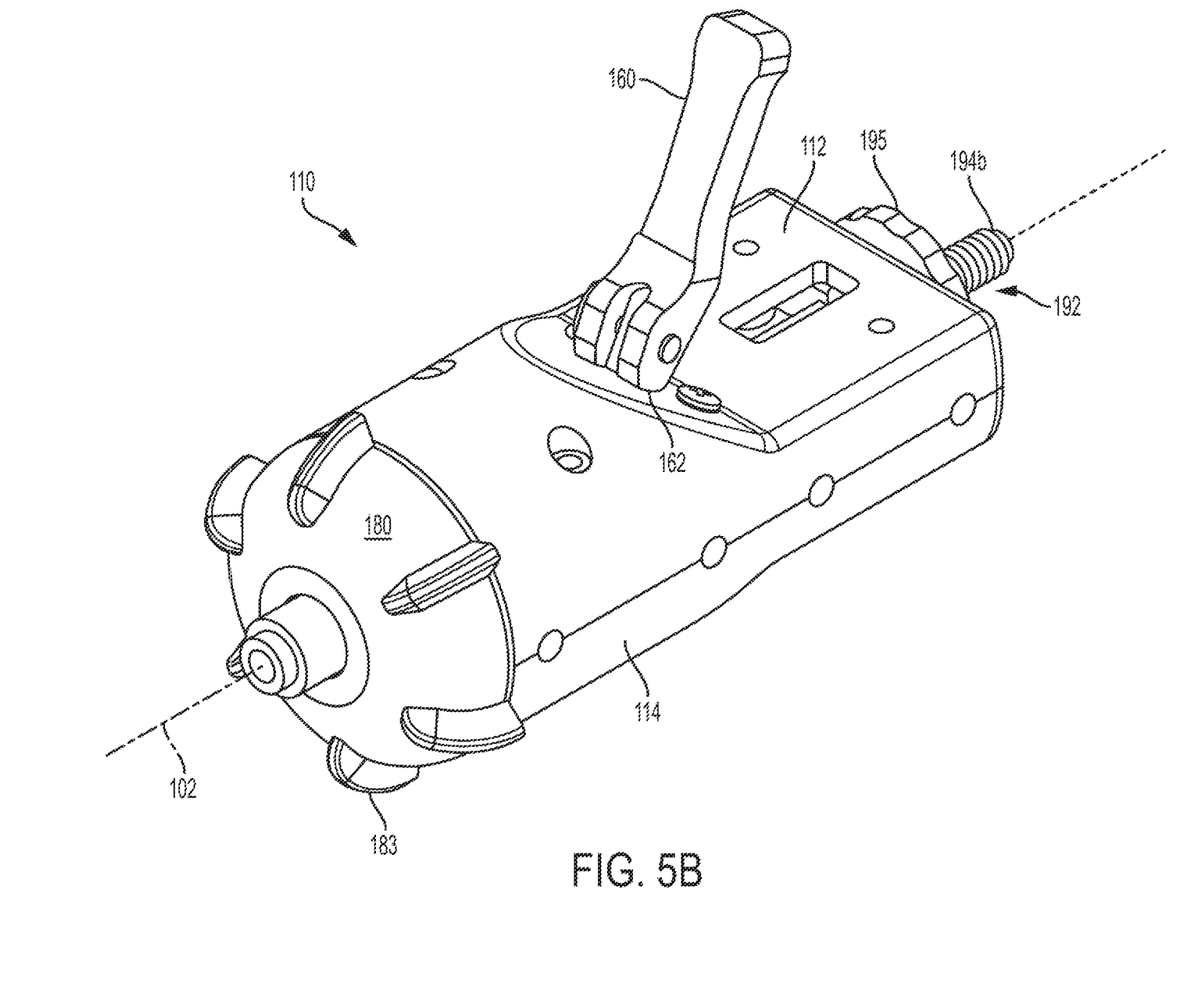

In the preferred embodiment shown, first and second steering cables 154 and 156 are wrapped around barrel portions 172 and 178, respectively, in a manner such that as tension is increased in one of the steering cables due to rotation of steering level 160, tension is lessened in the other steering cable. As such, first and second steering cables 154 and 156 work in unison to effect curvature of distal portion 132 to either the left or right direction of the previously discussed vertical plane. Specifically, when viewing sheath assembly 100 from above, rotation of steering lever 160 in the CW direction causes distal portion 132 of introducer sheath 130 to curve to the right, away from longitudinal center axis 102. Conversely, rotation of steering lever 160 in the CCW direction causes distal portion 132 of introducer sheath 130 to curve to the left, away from longitudinal center axis 102. Referring additionally to FIGS. 5A and 5B, steering lever 160 is shown in the un-locked portion, in which it is rotatable with respect to handle portion 110, and the locked position, in which it is non-rotatably secured to handle portion 110, respectively. By pivoting steering lever 160 upwardly from the un-locked position (FIG. 5A) to the locked position (FIG. 5B), camming surface 162 is caused to be frictionally engaged with the outer surface of handle portion 110. As such, drive gear 166 is similarly frictionally locked to the inner surface of the handle portion and the desired curvature of the introducer sheath distal portion 132 to the left or right of the vertical plane is maintained.

Still referring to FIGS. 2 and 7A, third steering cable 158 (FIG. 4) includes a distal end that is affixed to distal tip 136 of introducer sheath 130 and a proximal end that is affixed to threaded stem 188. As such, axial motion of threaded stem 188 causes the amount of curvature of distal portion 132 of the introducer sheath to be affected. Specifically, when viewing sheath assembly 100 from the rear, rotation of front end cap 180 in the CW direction causes axial motion of threaded stem rearwardly within handle portion 110. As such, the amount of tension placed on third steering cable 158 is increased and the amount of curvature present in distal portion 132 of the introducer sheath (referred to as "primary curvature") is increased. Conversely, rotation of front end cap 180 in the CCW direction causes threaded stem to move forwardly within handle portion 110, thereby reducing the amount of tension present in third steering cable 158. As such, the amount of curvature present in distal portion 132 of introducer sheath 130 is reduced. The amount of friction present between the threaded portions of front end cap 180 and threaded stem 188 provides a self-locking feature. In short, the amount of friction is great enough that when a user ceases rotation of front end cap 180, the amount of curvature present in distal portion 132 of introducer sheath 130 is maintained.

As shown in FIG. 3, introducer sheath 130 includes a guidewire notch 144 that extends radially inwardly from its outer surface until it intersects guidewire lumen 142, thereby separating guidewire lumen 142 into a distal portion 142a that extends along distal portion 132 of introducer sheath 130, and a proximal portion 142b that extends along proximal portion 134 of introducer sheath 130. In use, after guidewire 152 has been inserted into the patient in the desired position, introducer sheath 130 is inserted by running introducer sheath 130 along guidewire 152 as it is slidably received in guidewire lumen 142. After introducer sheath 130 is fully inserted into the patient, the user may withdraw guidewire 152 from introducer sheath 130 until the distal tip of guidewire 152 exits distal portion 132 of the sheath. Next, in order to stabilize the position of guidewire 152 within the patient, and therefore the position of introducer sheath 130, the user may advance guidewire 152 with its distal tip passing out of guidewire notch 144 and place the distal tip of guidewire 152 in the desired position. As such, guidewire notch 144 allows the user to firmly position guidewire 152, and therefore introducer sheath 130, within the patient, while allowing distal portion 132 of introducer sheath 130 to be readily manipulated using the previously discussed steering cables, without the guidewire inhibiting bending of the distal portion. With distal tip 136 of introducer sheath 130 in the desired position, the user may insert dilator 159 into device lumen 140 after passing the dilator through device locking assembly 192, as discussed in greater detail below.

Figure 6:
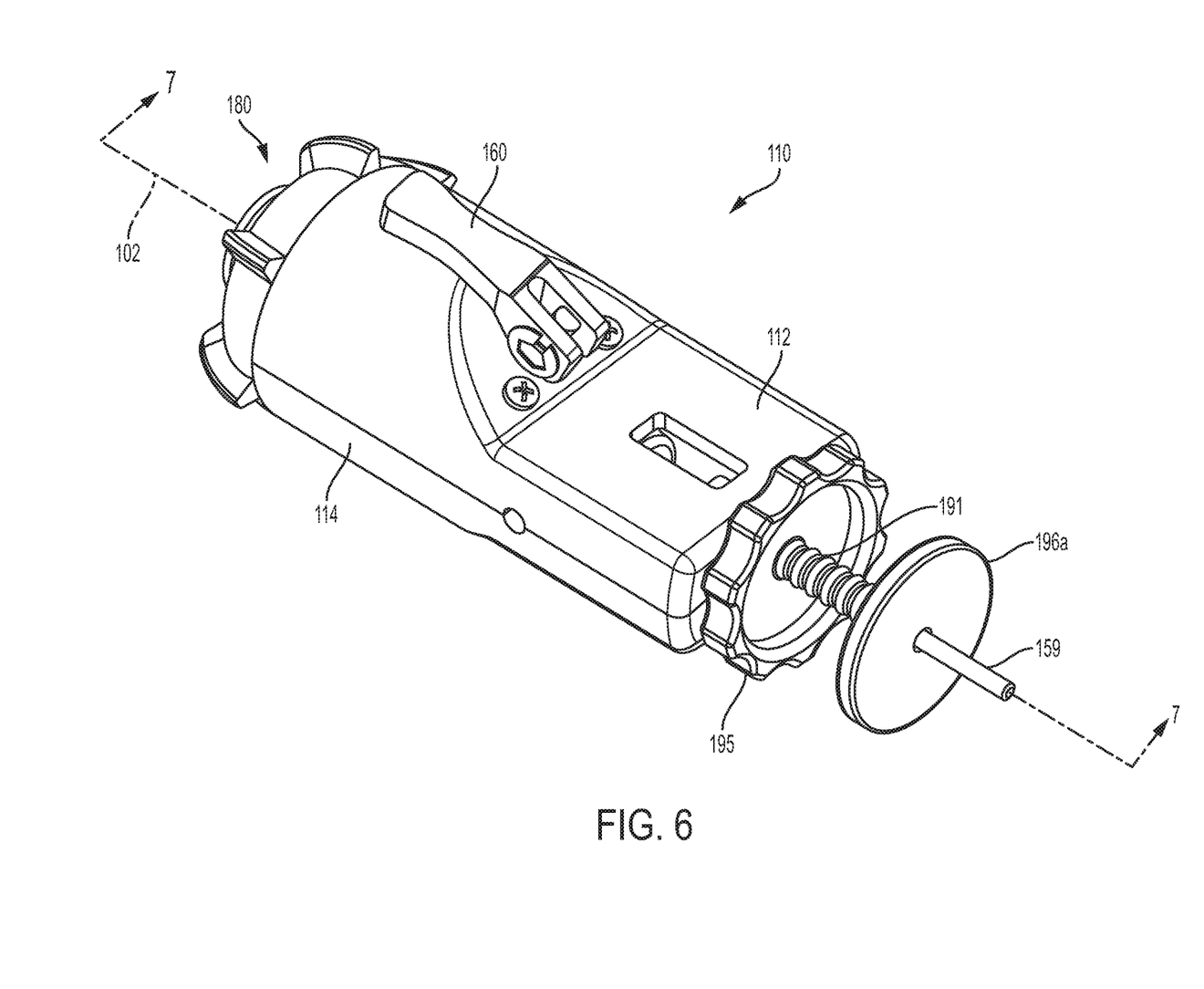
FIG. 6 is a top perspective view of the handle portion of the sheath assembly shown in FIG. 1.
Figure 7B:
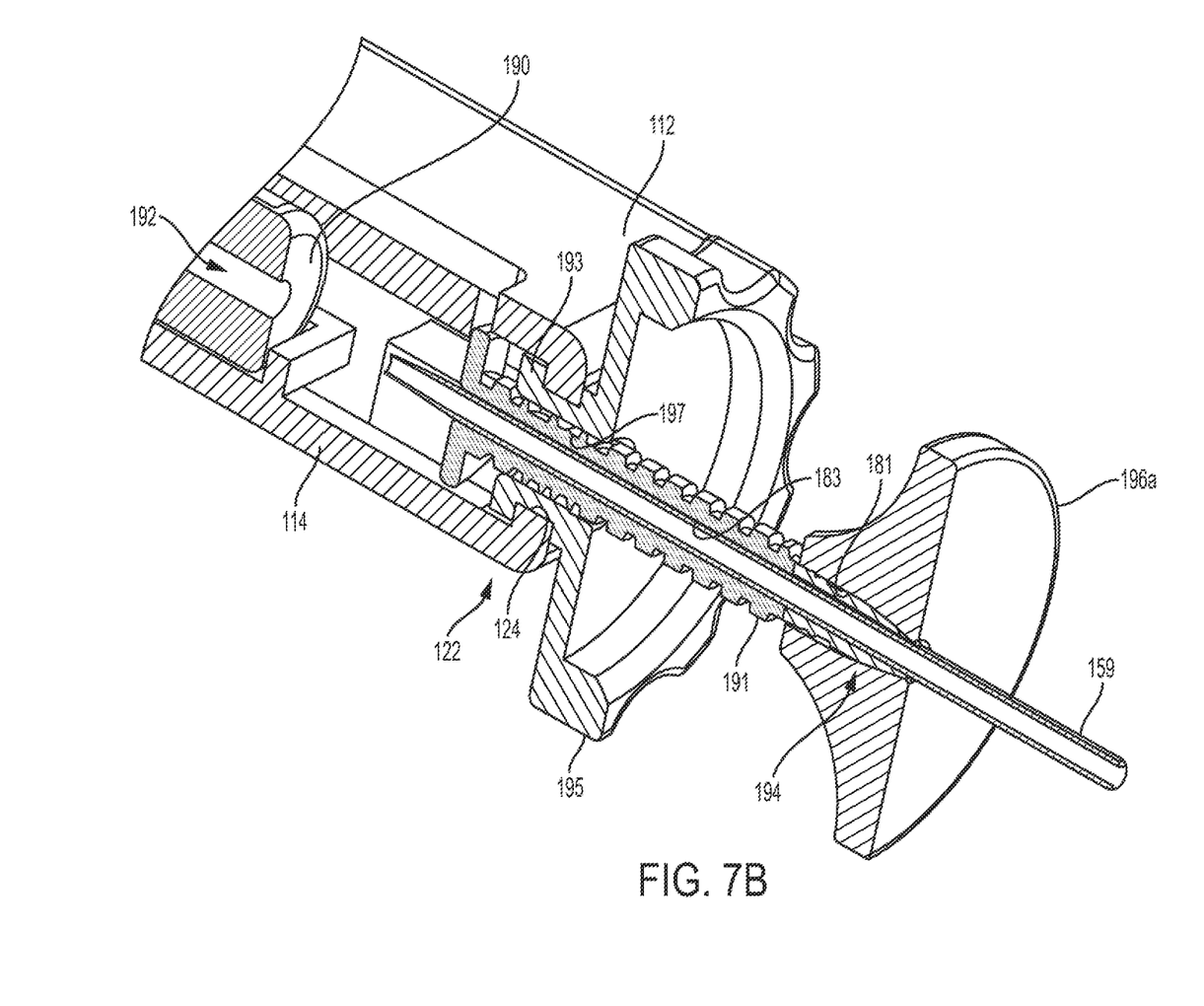

Referring now to FIGS. 6, 7A and 7B, device locking assembly 192 is disposed at rear end 122 of handle portion 110 and is configured to selectively fix the position of dilator 159 within introducer sheath 130. Device locking assembly 192 includes an advance knob 195 that is rotatably received within rear aperture 124 of handle portion 110, and retained therein by a flange 193 that extends radially outwardly from the front end of advance knob 195 and has a greater diameter than rear aperture 124. Advance knob 195 defines a threaded bore 197 that is correspondingly threaded to an outer surface of threaded stem 191, which is received therein. As shown, when viewing sheath assembly 100 from the rear, rotation of advance knob 195 in the CW direction causes threaded stem 191 to move outwardly from handle portion 110. Conversely, rotation of advance knob 195 in the CCW direction causes threaded stem 191 to move inwardly into handle portion 110. Note, however, in alternate embodiments, threaded stem 191 and advance knob 195 may include left-handed threading, meaning motion of the threaded stem would be inwardly when advance knob 195 is rotated in the CW direction and outwardly when rotated in the CCW direction.

As shown in FIGS. 6, 7A and 7B, a device lock is preferably provided in the form of a collet 194 formed by the rear end of the threaded stem 191, and a corresponding lock knob 196a which defines a frustoconical bore 181 that is configured to compress collet 194 inwardly on to a corresponding dilator 159, thereby axially fixing dilator 159 within threaded stem 191, and therefore within introducer sheath 130. Axially fixing dilator 159 within threaded stem 191 allows the user to exercise precise control over advancement of the dilator's distal tip by way of rotating advance knob 195. As such, operations such as puncturing the interatrial septum can occur in a very controlled manner. Conversely, when dilator 159 is not axially fixed within threaded stem 191, the user is free to advance and retract the dilator in an unimpeded fashion.

In the embodiment shown, both the outer surface of collet 194 and frustoconical bore 181 are formed by smooth surfaces, such that collet may be engaged by lock knob 196a by simply urging the lock knob over the collet. In an alternate embodiment, shown in FIGS. 1, 2, 5A and 5B, device locking assembly 192 includes a collet 194b having a threaded outer surface, which is engaged by a lock nut 196b which includes a threaded frustoconical bore (not shown). This second embodiment differs primarily from the first embodiment in that lock nut 196b threadably engages collet 194b to fix dilator 159 in the desired position.

A hemostatic introducer valve 190 is disposed within handle portion 110 between device locking assembly 192 and the proximal end of introducer sheath 130. A bore 182 of hemostatic introducer valve 190 guides the distal end of the catheter device into device lumen 140 of introducer sheath 130 while minimizing the likelihood of the introduction of air.

Figure 8:
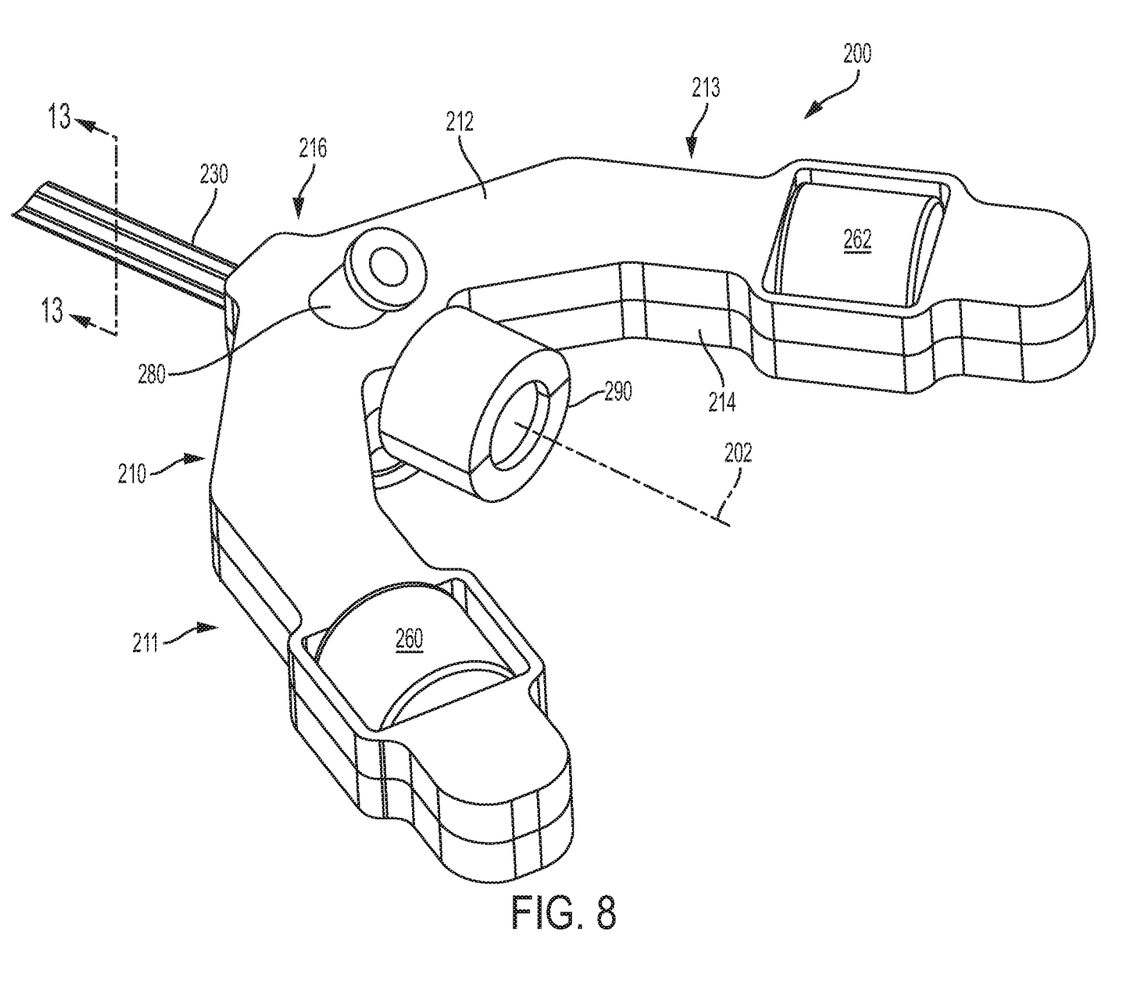
FIG. 8 is a top perspective view of an alternate embodiment of a steerable introducer sheath assembly in accordance with the present disclosure.
Figure 9:
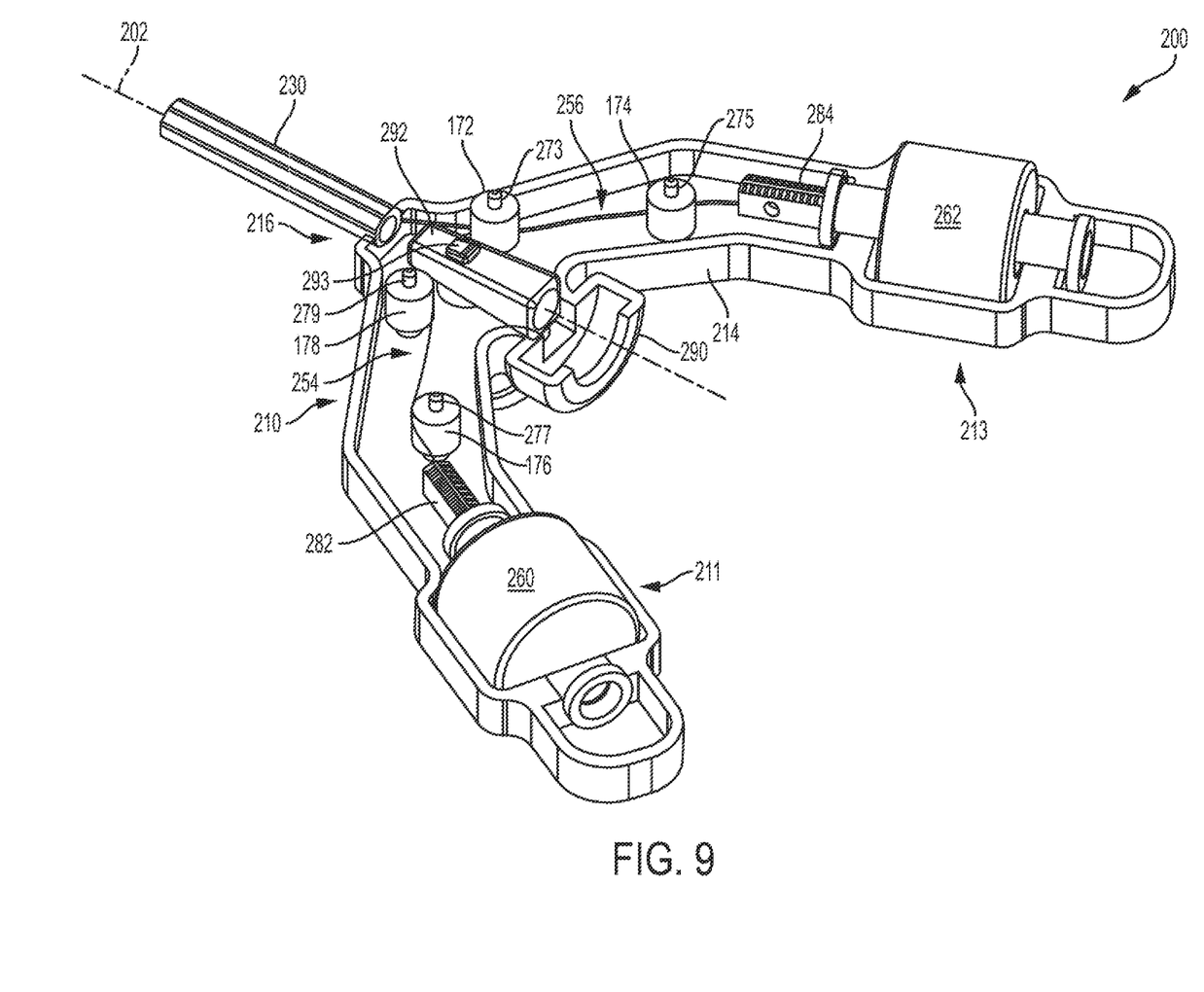
FIG. 9 is a top perspective view of the sheath assembly shown in FIG. 8, with the upper portion of the handle housing removed.

Referring now to FIGS. 8 and 9, an alternate embodiment of a steerable introducer sheath assembly 200 in accordance with the present disclosure is shown. Sheath assembly 200 includes a handle portion 210 constructed of an upper portion 212, a lower portion 214, and has an elongated, octagonally shaped introducer sheath 230 (truncated in FIGS. 1 and 2 for illustrative purposes) extending from its front end 216. Handle portion 210 includes two wing portions 211 and 213 extending symmetrically at a specified angle to provide mechanical/geometric differentiation to the user. A first and a second thumbwheel 260 and 262, respectively, are present in each wing portion 211 and 213, respectively, and can be manipulated by the user to selectively increase and decrease tension on a first and a second steering cable 254 and 256, respectively, thereby deflecting a distal portion 232 of introducer sheath 230. A hemostatic introducer valve 290 is disposed on the rear end of handle portion 210 which allows other medical devices to be inserted into and retracted from introducer sheath 230 while minimizing the likelihood of air introduction into the saline flushed system.

A flushing port/guidewire luer 280 extends outwardly from upper portion 212 of handle portion 210, and is configured to receive a rotating hemostatic valve (not shown). The rotating hemostatic valve allows the user to selectively tighten and release introducer sheath 230 from a guidewire 252 (FIG. 13), thereby allowing introducer sheath 230 to torque and translate relative to the guidewire, while minimizing the chance and amount of air introduction into the system.

Handle portion 210 is sufficiently narrow enough to comfortably fit within a user's hand. The materials used in constructing handle portion 210 are preferably high strength plastics suitable for medical device purposes, and may be clear to permit evaluation of de-airing of handle portion 210 using a saline flush during device preparation. Such materials can be, but are not limited to, polycarbonates, acrylics, acrylonitrite butadiene styrene (ABS) and polyurethanes.

Preferably, introducer sheath 230 is composed of a suitable high strength, biocompatible polymer that is extrudable and has an established history of use in medical devices. The preferred polymers should also permit a variety of secondary manufacturing processes that may be desired to enhance both performance and durability of the sheath. Some of these secondary manufacturing processes may include thermoforming, bonding, fusing, braiding, cutting, machining, forming, heat shrinking, stamping, labeling, and hydrophilically coating, and example polymers are, but are not limited to, polyurethanes, fluoropolymers, polyolefins, polyimides, polyvinyl chloride (PVC) and polyether ether ketone (PEEK).

Referring now to FIG. 9, lower portion 214 of handle portion 210 is shown with upper portion 212 removed, thereby revealing the inner components of sheath assembly 200. Four bearing cylinders 272, 274, 276, and 278 are rotatably received about four axles 273, 275, 277 and 279, respectively. Bearing cylinders 272, 274, 276 and 278 provide a low friction bearing surface and define a path of travel for first and second steering cables 254 and 256. First and second steering cables 254 and 256 are mechanically attached to first and second translating screws 282 and 284, respectively, and travel through corresponding lumens of the introducer sheath 230, as discussed in greater detail below. First and second translating screws 282 and 284 are received in correspondingly threaded bores of first and second thumbwheels 260 and 262, respectively. As such, rotation of first and second thumbwheels 260 and 262 increases and decreases the amount of tension on first and second steering cables 254 and 256, respectively, as first and second translating screws 282 and 284 move into and out of the threaded bores. The distal ends of first and second steering cables 254 and 256 are attached mechanically or adhesively to a distal tip 236 of introducer sheath 230.

Bearing cylinders 272, 274, 276 and 278 are preferably made from a low friction polymer to minimize friction between the surfaces of both first and second steering cables 254 and 256, and the corresponding axles. Axles 273, 275, 277 and 279 are preferably made from a high strength metal alloy suitable for medical device purposes and will have a diameter large enough to provide enough strength to withstand the force placed on them when the required tension in the steering cables is applied.

Preferably, a funnel 292 is used to direct inserted catheter device 159 from hemostatic introducer valve 290 into the appropriate device lumen 240 of introducer sheath 230. Funnel 292 may also have a ramped-shaped feature 293 on its top side which biases or influences guidewire 252 (FIG. 13) to exit up and into the guidewire luer 280 as introducer sheath 230 is passed along guidewire 252 which has been previously routed to the desired position within the patient, as previously discussed.

Figure 10:
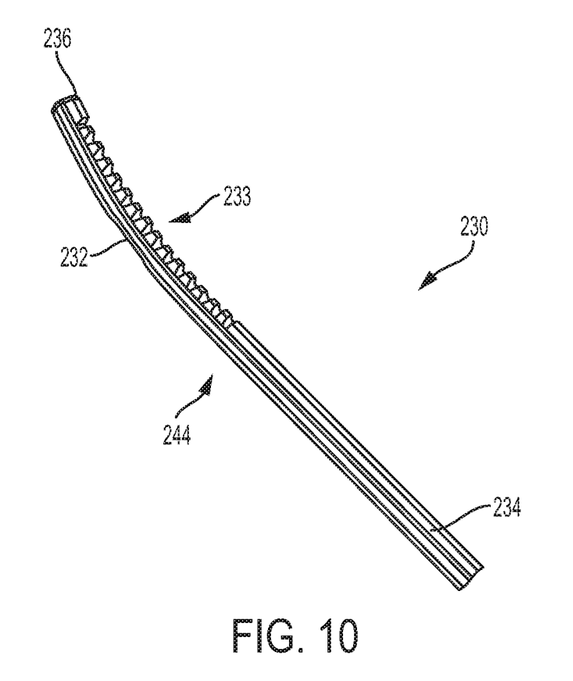
FIG. 10 is a perspective view of the distal end of the introducer sheath of the sheath assembly shown in FIG. 8.
Figure 11:
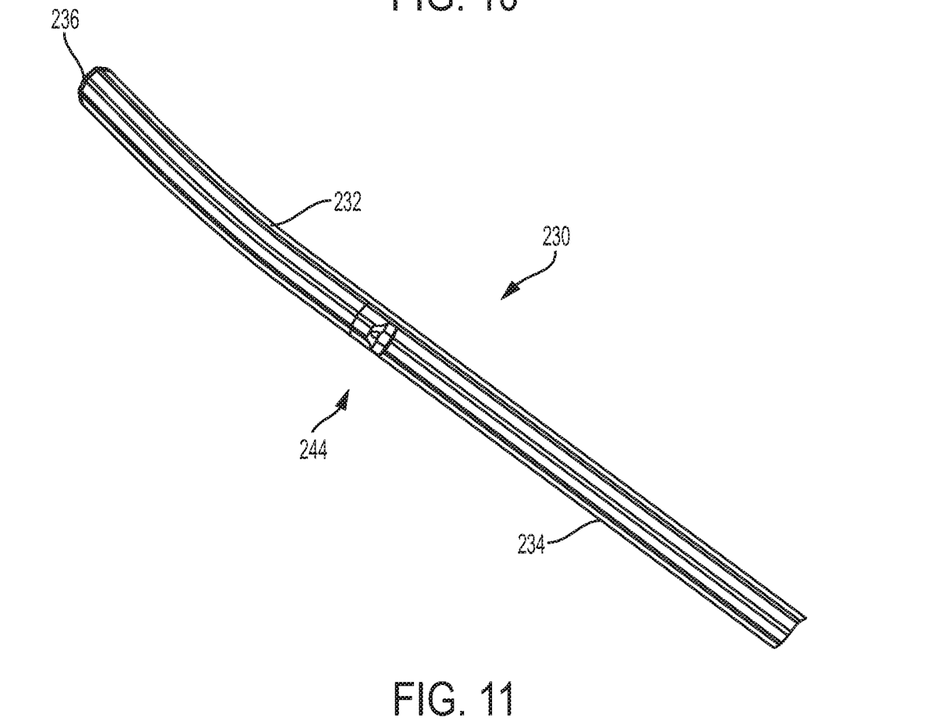
FIG. 11 is a bottom perspective view of the distal end of the introducer sheath of the sheath assembly shown in FIG. 8.
Figure 12:
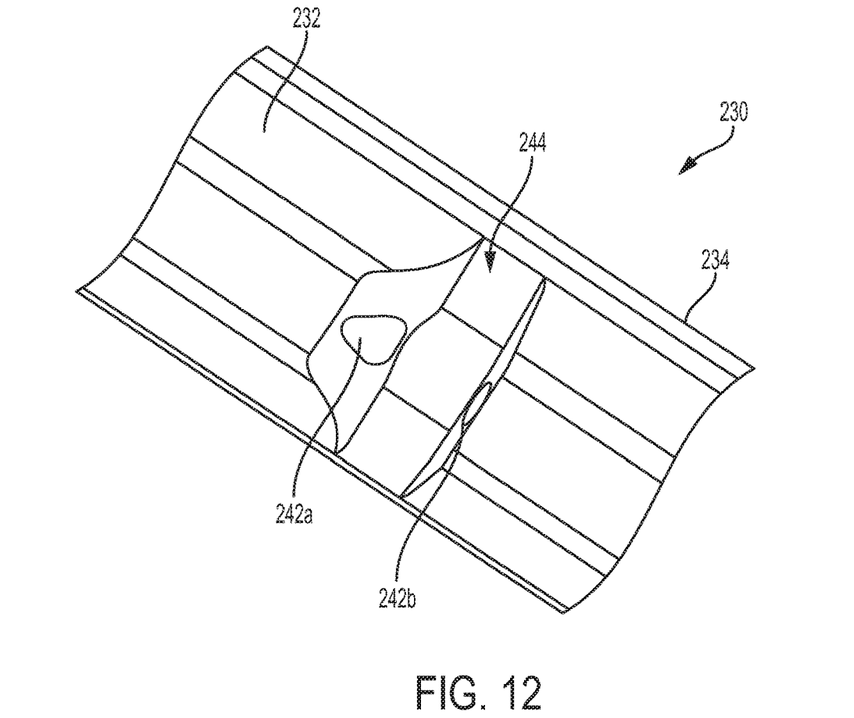
FIG. 12 is an exploded, detailed view of the guidewire notch of the introducer sheath shown in FIGS. 10 and 11.

Referring now to FIGS. 10 and 11, an enlarged view of the distal end of introducer sheath 230 is shown. Mechanical deflection notches 233 are formed in distal portion 232 of the sheath to permit a controlled deflection of distal portion 232 relative to proximal portion 234 of introducer sheath 230 as tension on first and second steering cables 254 and 256 is increased. As best seen in FIG. 12, a magnified view of a guidewire notch 244 is provided, guidewire notch 244 being disposed opposite the deflection notches. As in the previously discussed embodiment of the sheath assembly, guidewire notch 244 divides guidewire lumen 242 into a distal portion 242a and a proximal portion 242b. Guidewire notch 244 is designed such that when guidewire 252 (FIG. 13) is backloaded into introducer sheath 230 upon introduction into the vasculature of the patient, guidewire 252 traverses guidewire notch 244 and connects distal potion 242a to proximal portion 242b of guidewire lumen 242. This permits introducer sheath 230 to safely track over guidewire 252 to its desired location. However, once the introducer sheath is generally located, guidewire notch 244 is designed such that when the distal end of guidewire 252 is retracted past the notch into proximal portion 242b of guidewire lumen 242, then readvanced, the distal end of guidewire 252 escapes the distal portion 242a of the guidewire lumen and frees itself from the deflectable distal portion 232 of introducer sheath 230. This feature permits guidewire 252 to stay in place and continue to provide mechanical stability to the system without restricting the ability of the distal portion of the introducer sheath 230 from deflecting when manipulated.

Figure 13:
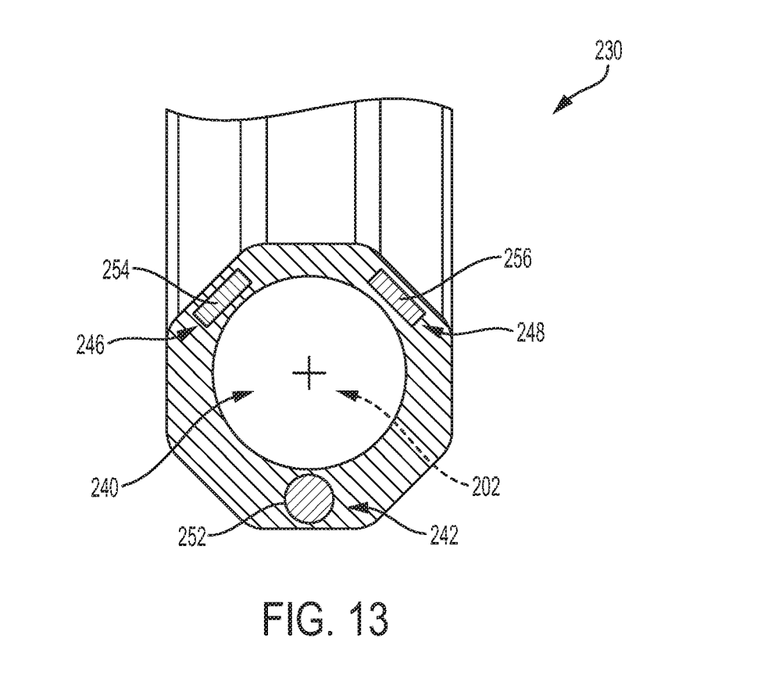
FIG. 13 is a cross-sectional view of the introducer sheath of the sheath assembly shown in FIG. 8, taken along line 13-13.

Referring now to FIG. 13, a cross-sectional view of the octagonally-shaped introducer sheath 230 taken along line 13-13 of FIG. 8 is provided. As shown, first and second steering cable lumens 246 and 248 are rectangularly-shaped and configured to receive corresponding shaped first and second steering cables 254 and 256. Also shown is guidewire lumen 242 and the larger diameter device lumen 240. Preferably, the outer profile of introducer sheath 230 is shaped like an octagon to minimize device dimensions as well as assist the user in determining the orientation of introducer sheath 230 within patient's body.

Still referring to FIG. 13, the orientations of first and second steering cable lumens 246 and 248 within the walls of introducer sheath 230 are such that when tension is applied to cables 254 and 256 which travel through them, the introducer sheath deflects in a specific, repeatable curving plane relative to guidewire lumen 242, about which the introducer sheath is translating/rotating. The rectangular cross-sectional shape of first and second steering cables 254 and 256 provide enough cross-sectional area to be strong enough in tension to deflect the distal end, while minimizing the cross-sectional area in a specific dimension to help reduce overall cross-sectional diameter of introducer sheath 230. As well, first and second steering cables 254 and 256 are also oriented in such a manner such that their bending moment of inertia is minimized in an orientation so that the cables are flexible in bending, thereby making the system more deliverable and trackable through tortuous anatomy.

While one or more preferred embodiments of the invention are described above, it should be appreciated by those skilled in the art that various modifications and variations can be made in the present invention without departing from the scope and spirit thereof. It is intended that the present invention cover such modifications and variations as come within the scope and spirit of the appended claims and their equivalents.

What is claimed:

1. An introducer sheath assembly comprising:
 a handle portion including a front end and a rear end;
 a first gear assembly including a first gear having a first plurality of teeth;
 a second gear assembly including a second gear having a second plurality of teeth, and a third gear assembly including a third gear having a third plurality of teeth, wherein the first, second gear assembly, and third gear assembly are disposed in the handle portion, and the third plurality of teeth of the third gear assembly engages both the first plurality of teeth of the first gear assembly and the second plurality of teeth of the second gear assembly, and the first gear assembly, second gear assembly, and third gear assembly are configured to rotate simultaneously;
 an introducer sheath extending outwardly from the front end of the handle portion, the introducer sheath including,
 a device lumen configured to slidably receive a corresponding device,
 a first steering cable lumen, and a second steering cable lumen, and
 a first steering cable disposed in the first steering cable lumen, and a second steering cable disposed in the second steering cable lumen,
 wherein a proximal end of the first steering cable is fixed to the first gear assembly so that a portion of the first steering cable is wrapped around a portion of the first gear assembly, a proximal end of the second steering cable is fixed to the second gear assembly so that a portion of the second steering cable is wrapped around a portion of the second gear assembly, and a distal end of the first steering cable and a distal end of the second steering cable are fixed to a distal end of the introducer sheath, and
 the first gear assembly includes a cylindrical barrel portion extending outwardly from the first gear and includes a cylindrical outer surface, the second gear assembly includes a cylindrical barrel portion extending outwardly from the second gear and includes a cylindrical outer surface, and the portion of the first steering cable is wrapped around the cylindrical outer surface of the barrel portion of the first gear assembly and the portion of the second steering cable is wrapped around the cylindrical outer surface of the barrel portion of the second gear assembly.

2. The introducer sheath assembly of claim 1, further comprising a lever disposed on an outer surface of the handle portion, wherein the lever is non-rotatably fixed to the third gear assembly so that rotation of the lever causes rotation of the third gear assembly.

3. The introducer sheath assembly of claim 2, wherein the lever is positionable between a locked position in which the lever is non-rotatably fixed to the handle portion and an unlocked position in which the lever is rotatable relative to the handle portion.

4. The introducer sheath assembly of claim 1, wherein the first and the second steering cable lumens are disposed on opposing sides of a vertical plane in which a longitudinal center axis of the introducer sheath lies.

5. The introducer sheath assembly of claim 4, wherein a cross-sectional shape of the first steering cable lumen and the second steering cable lumen in a vertical plane transverse to the longitudinal center axis of the introducer sheath is rectangular.

6. The introducer sheath assembly of claim 1, wherein a cross-sectional shape of the introducer sheath in a vertical plane transverse to a longitudinal center axis of the introducer sheath is a geometric shape.

7. The introducer sheath assembly of claim 6, wherein the geometric shape is octagonal.

8. The introducer sheath assembly of claim 1, wherein the corresponding device slidably received in the device lumen is a dilator, the dilator defining an elongated bore.

9. The introducer sheath assembly of claim 1, further comprising:
- a guidewire lumen configured to slidably receive a corresponding guidewire, and
- a guidewire notch extending radially inwardly from an outer surface of the introducer sheath and intersecting the guidewire lumen so that the guidewire lumen is formed by a first portion and a second portion, the first portion extending along a deflectable tip portion of the introducer sheath.

10. An introducer sheath assembly comprising:
a handle portion including a front end and a rear end;
an introducer sheath extending outwardly from the front end of the handle portion, the introducer sheath including a device lumen configured to slidably receive a corresponding device, a first steering cable lumen, a first steering cable disposed in the first steering cable lumen, a second steering cable lumen, and a second steering cable disposed in the second steering cable lumen;
a first gear assembly including a first gear having a first plurality of teeth and a first barrel portion, the first gear assembly being disposed entirely within the handle portion, a proximal end of the first steering cable being fixed to the first barrel portion of the first gear assembly so that the proximal end of the first steering cable is wrapped around the first barrel portion; and
a second gear assembly including a second gear having a second plurality of teeth and a second barrel portion, the second gear assembly being disposed entirely within the handle portion, a proximal end of the second steering cable being fixed to the second barrel portion of the second gear assembly so that the proximal end of the second steering cable is wrapped around the second barrel portion;
a drive gear assembly disposed entirely within the handle portion, wherein the drive gear assembly includes a third gear having a third plurality of teeth, wherein the third plurality of teeth engages the first plurality of teeth of the first gear assembly and the second plurality of teeth of the second gear assembly, and the first gear assembly, the second gear assembly, and the drive gear assembly are configured to rotate simultaneously.

11. The introducer sheath assembly of claim 10, wherein a distal end of the first steering cable and a distal end of the second steering cable are fixed to a distal end of the introducer sheath.

12. The introducer sheath assembly of claim 11, further comprising;
a third steering cable lumen; and
a third steering cable disposed in the third steering cable lumen,
wherein the first steering cable lumen, the second steering cable lumen and the third steering cable lumen are disposed radially outwardly from the device lumen.

13. The introducer sheath assembly of claim 10, further comprising a lever disposed on an outer surface of the handle portion, wherein the lever is non-rotatably fixed to the drive gear assembly so that rotation of the lever causes rotation of the drive gear assembly.

14. The introducer sheath assembly of claim 13, wherein the lever is positionable between a locked position in which the lever is non-rotatably fixed to the handle portion and an unlocked position in which the lever is rotatable relative to the handle portion.

15. The introducer sheath assembly of claim 10, further comprising a guidewire lumen configured to slidably receive a corresponding guidewire, wherein the guidewire lumen is disposed radially outwardly from the device lumen.

16. The introducer sheath assembly of claim 15, wherein a guidewire notch extends radially inwardly from an outer surface of the introducer sheath and intersects the guidewire lumen so that the guidewire lumen is formed by a first portion and a second portion, the first portion extending along a deflectable tip portion of the introducer sheath.

17. The introducer sheath assembly of claim 10, wherein the corresponding device slidably received in the device lumen is a dilator, the dilator defining an elongated bore.

18. An introducer sheath assembly comprising:
a handle portion including a front end and a rear end;
an introducer sheath extending outwardly from the front end of the handle portion, the introducer sheath including a device lumen configured to slidably receive a corresponding device; and
a device locking assembly disposed at the rear end of the handle portion, including,
an elongated stem having an outer surface including a threaded portion, and
a proximal end extending outwardly from the rear end of the handle portion, the elongated stem defining an axially extending bore that is configured to slidably receive the corresponding device, the elongated stem being axially movable with respect to the handle portion,
an advance knob including a threaded bore that is threadably engaged with the threaded portion of the elongated stem, the advance knob being both axially fixed and rotatable with respect to the handle portion; and
a clamp disposed at the proximal end of the elongated stem outside of the handle portion, the clamp being positionable between a locked position in which the corresponding device is axially fixed with respect to the elongated stem and an un-locked position in which the corresponding device is slidable within the axially extending bore of the elongated stem,
wherein the clamp further comprises a collet formed by the proximal end of the elongated stem so that the collet is both axially-fixed to, and non-rotatable with respect to, the elongated stem, and a locking knob defines a frustoconical bore that is engaged with the collet, and an outer surface of the collet of the elongated stem and an inner surface of the frustoconical bore of the locking knob are correspondingly threaded.

* * * * *

UNITED STATES PATENT AND TRADEMARK OFFICE
CERTIFICATE OF CORRECTION

PATENT NO. : 11,534,579 B2
APPLICATION NO. : 14/987272
DATED : December 27, 2022
INVENTOR(S) : Jaime Eduardo Sarabia et al.

It is certified that error appears in the above-identified patent and that said Letters Patent is hereby corrected as shown below:

In the Specification

In Column 1, Line 42, delete "ineteratrial" and insert --interatrial--.

In Column 1, Lines 52-53, delete "transephogeal" and insert --transesophageal--.

In Column 4, Line 47, delete "transeptal" and insert --transseptal--.

In Column 4, Line 49, delete "transeptal" and insert --transseptal--.

In Column 8, Line 8, delete "acrylonitrite" and insert --acrylonitrile--.

Signed and Sealed this
Thirtieth Day of May, 2023

Katherine Kelly Vidal
*Director of the United States Patent and Trademark Office*